(12) United States Patent
Ebner

(10) Patent No.: US 6,428,826 B1
(45) Date of Patent: Aug. 6, 2002

(54) CHILCO PRODUCT AND METHOD OF MAKING AND USING SAME

(75) Inventor: Raquel Alvarez Ebner, Aysen (CL)

(73) Assignee: bioActiva microtechne, Lonetree, CO (US)

( * ) Notice: Subject to any disclaimer, the term of this patent is extended or adjusted under 35 U.S.C. 154(b) by 0 days.

(21) Appl. No.: 09/680,838

(22) Filed: Oct. 6, 2000

Related U.S. Application Data
(60) Provisional application No. 60/158,203, filed on Oct. 7, 1999.

(51) Int. Cl.⁷ .................................................. A61K 35/78
(52) U.S. Cl. ....................................................... 424/778
(58) Field of Search .................................. 424/725, 778

(56) References Cited

PUBLICATIONS

Computer Abstract Caba Rodriquez et al Phytotherapy Res (1994) vol. 8 No. 3 pp. 157–160.*

* cited by examiner

*Primary Examiner*—Herbert J. Lilling
(74) *Attorney, Agent, or Firm*—Sheridan Ross P.C.

(57) ABSTRACT

The Chilean Chilco plant, and extracts therefrom, is used to generate particular formulations having use medicinally as a diuretic, anti-pyretic and principally as a regulator of female menstruation. Other aspects of the invention include the use of Chilco extracts as enhancers of sexual function in both male and females.

5 Claims, 13 Drawing Sheets

Figures 1, 2:
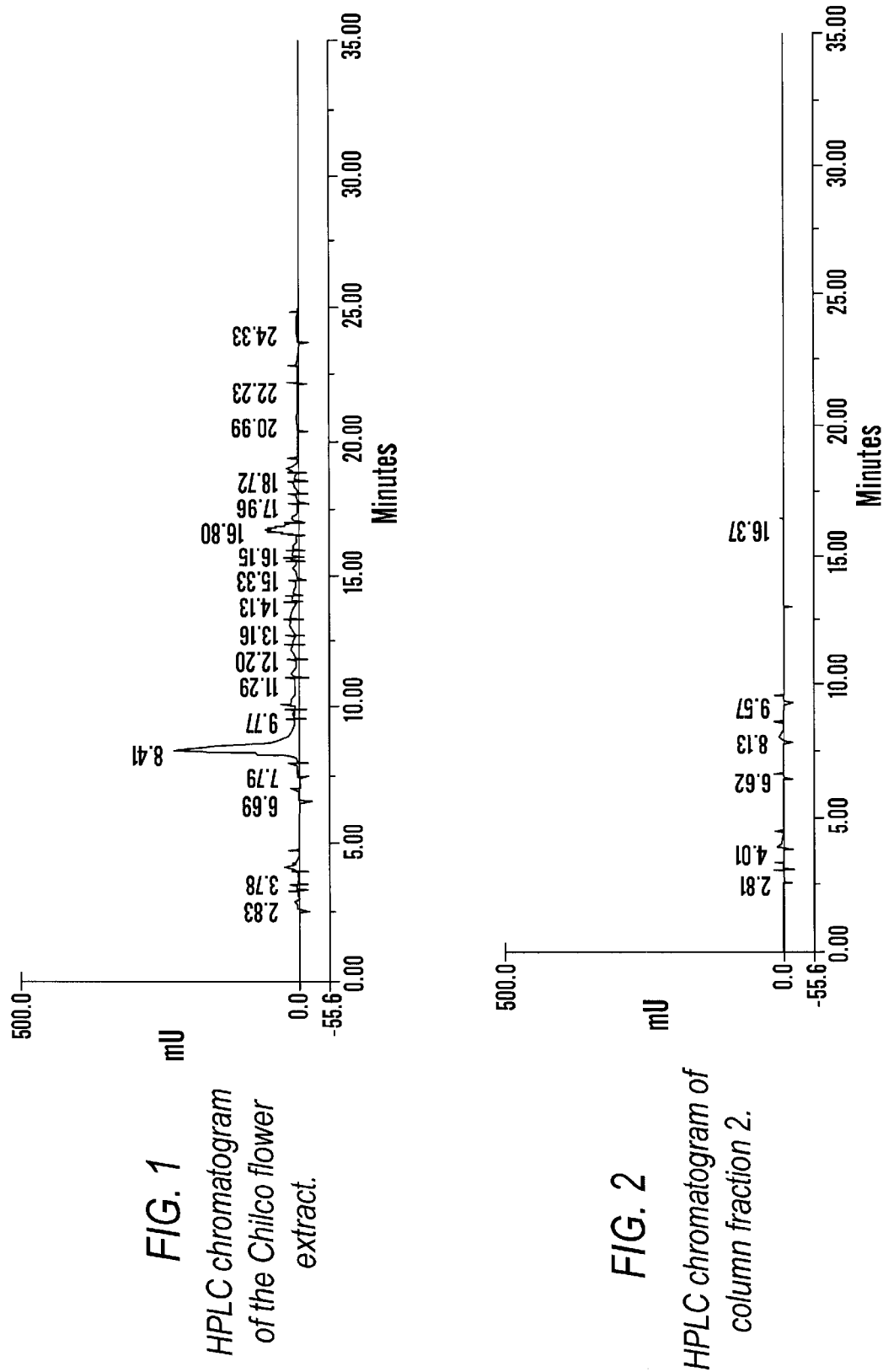
Figures 3, 4:
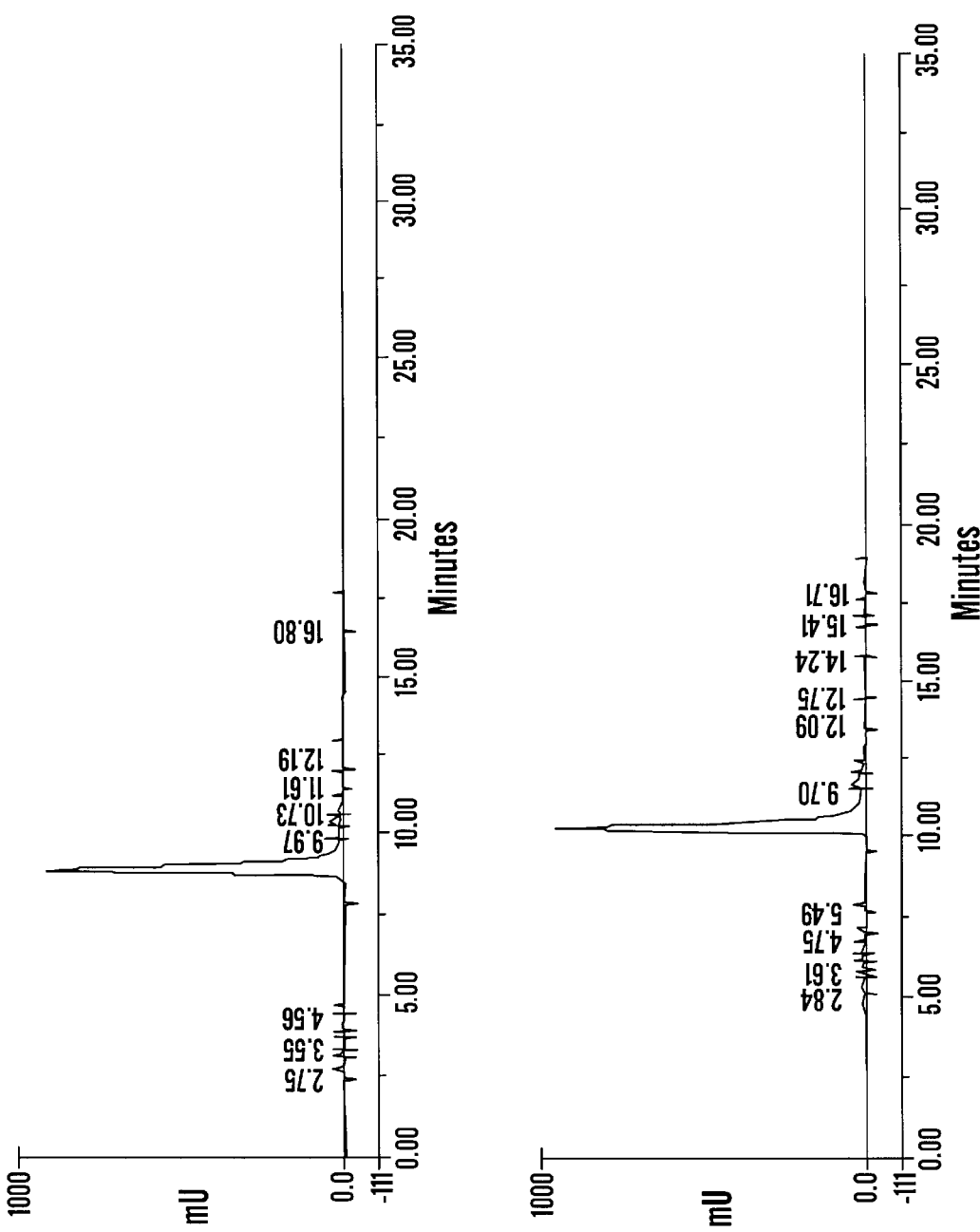
Figure 5:
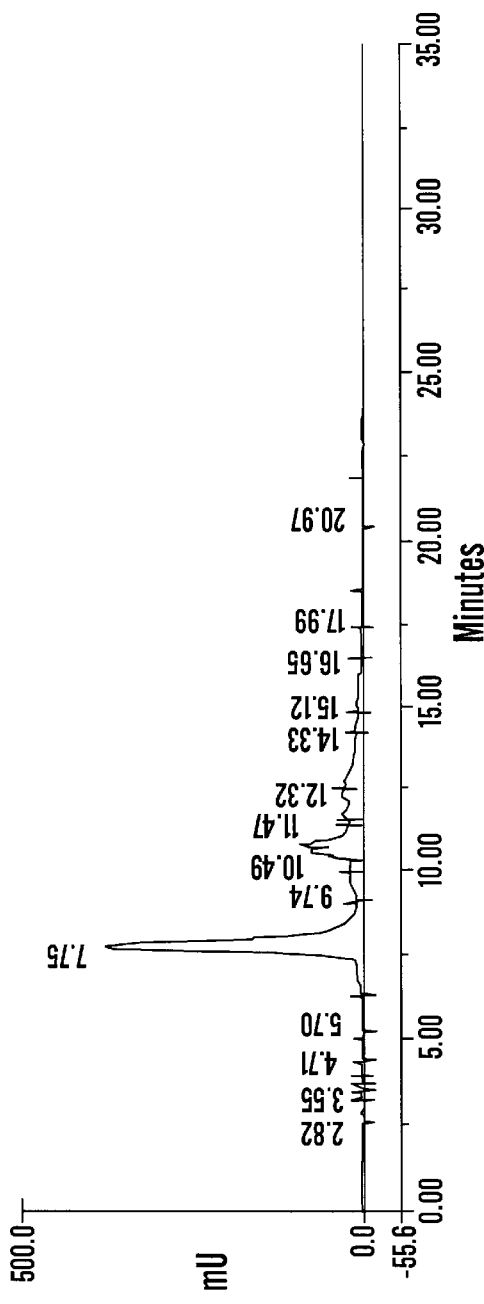
Figure 6:
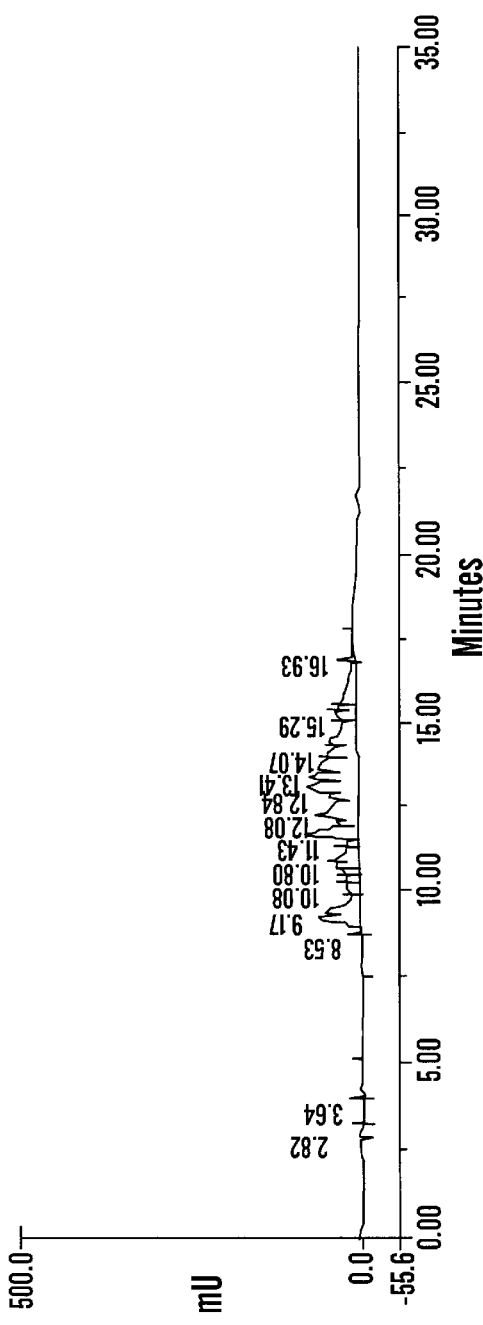
Figure 7:
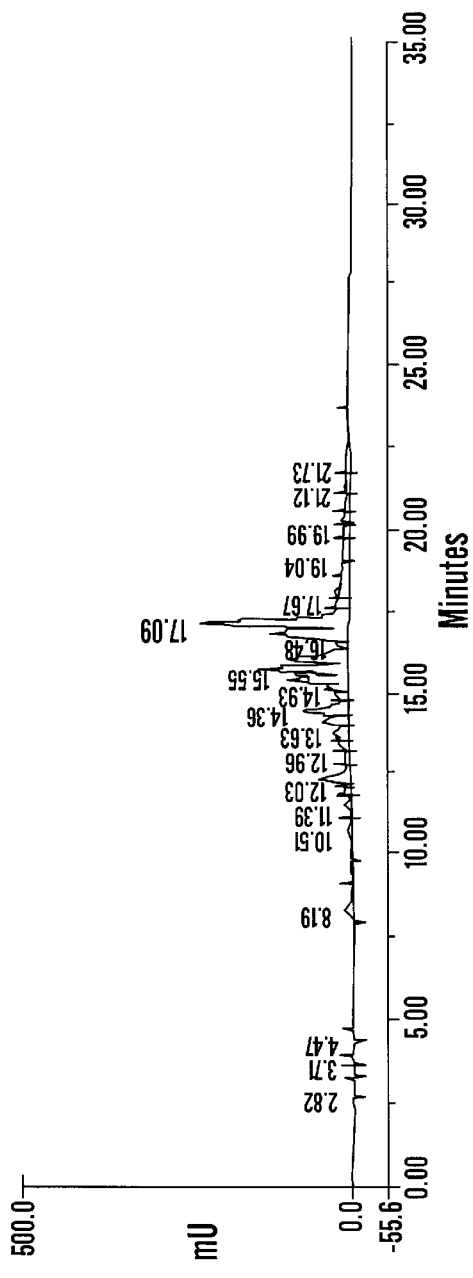
Figure 8:
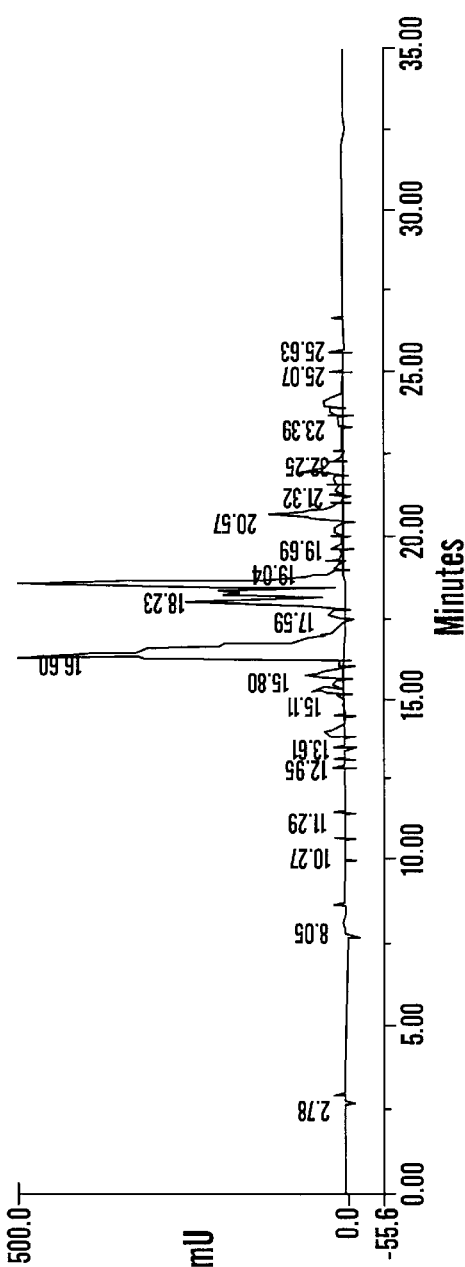

HPLC chromatogram of the Chilco flower extract.

HPLC chromatogram of column fraction 2.

HPLC chromatogram of column fraction 3.

HPLC chromatogram of column fraction 4.

HPLC chromatogram of column fraction 5.

HPLC chromatogram of column fraction 6.

HPLC chromatogram of column fraction 6.

HPLC chromatogram of column fraction 8.

HPLC chromatogram of column fraction 9.

HPLC chromatogram of column fraction 10.

HPLC chromatogram of column fraction 11.

HPLC chromatogram of column fraction 12.

Mass spectrum of column fraction 3.

Figure 14:
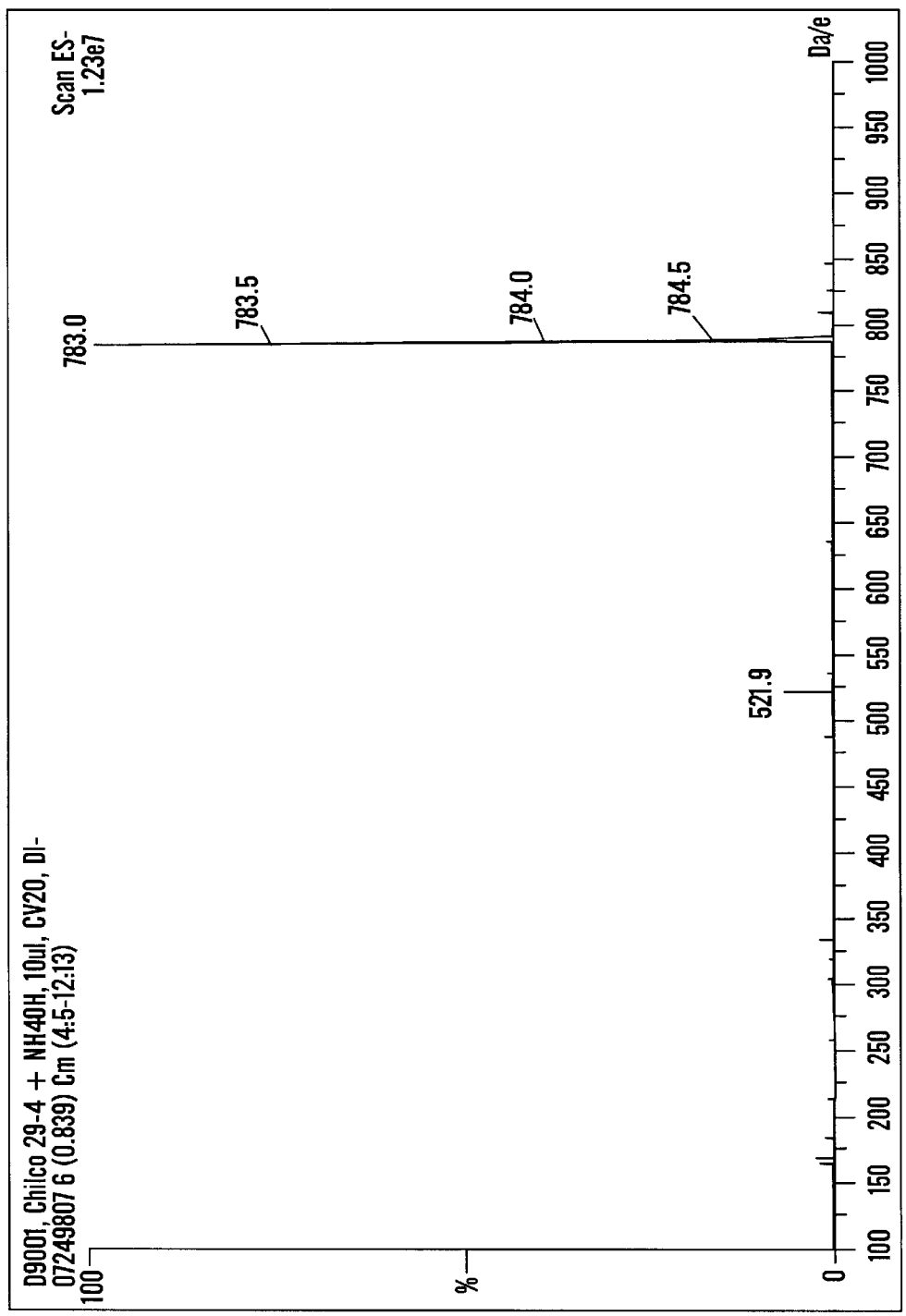
Figure 15:
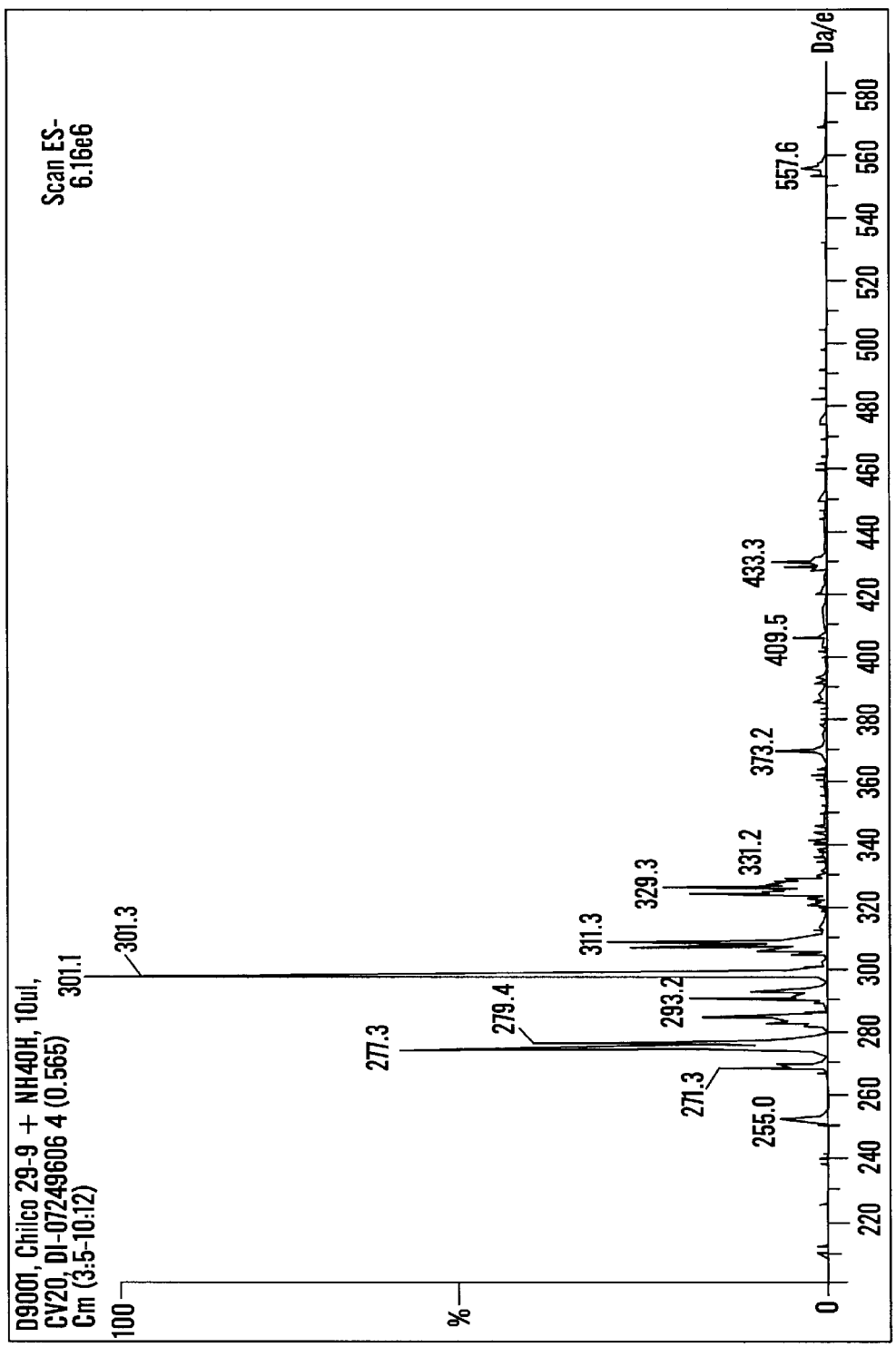
Figure 16:
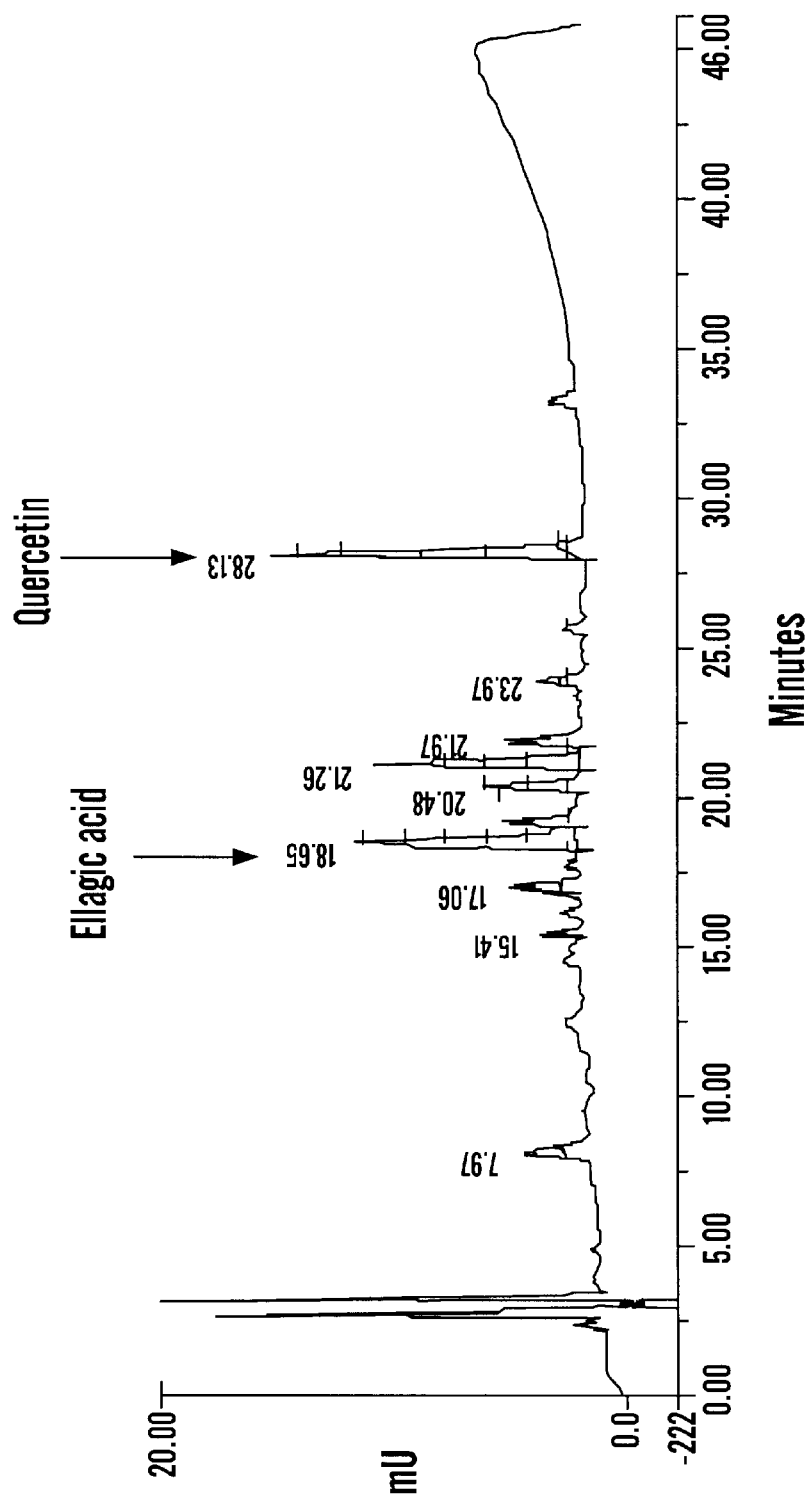
Figure 17:
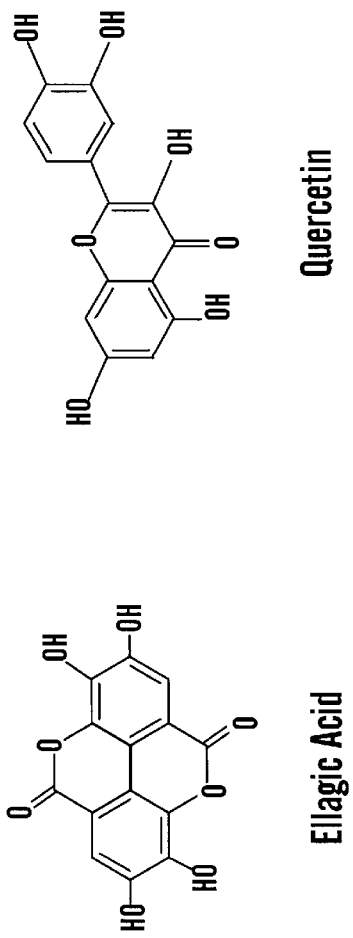
Figure 18:
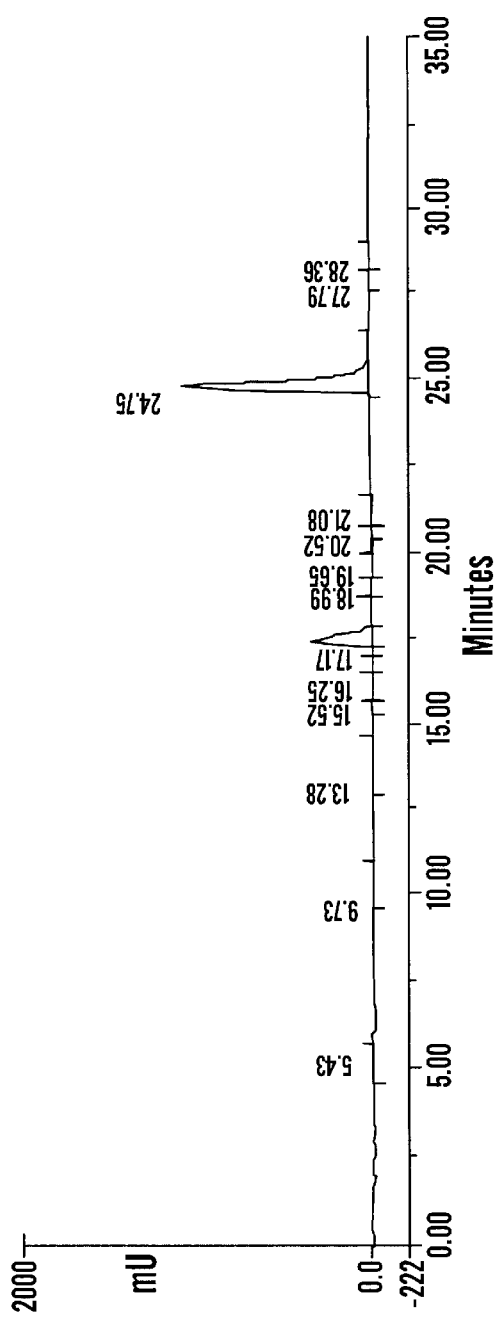
Figure 19:
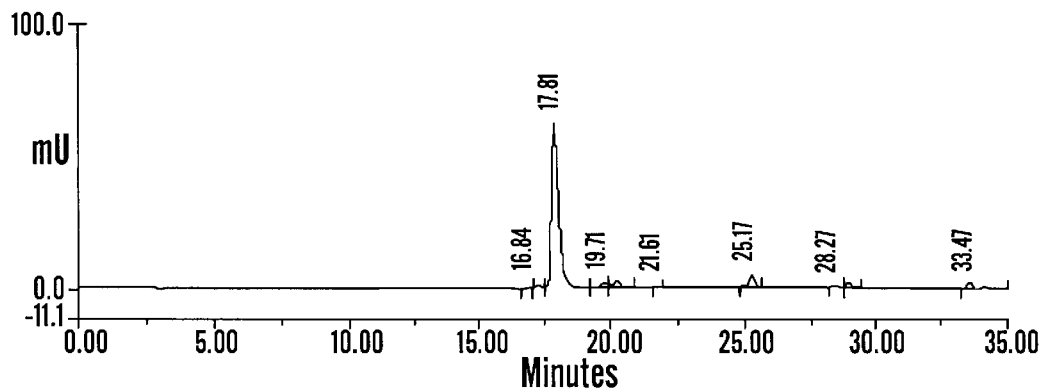
Figure 20:
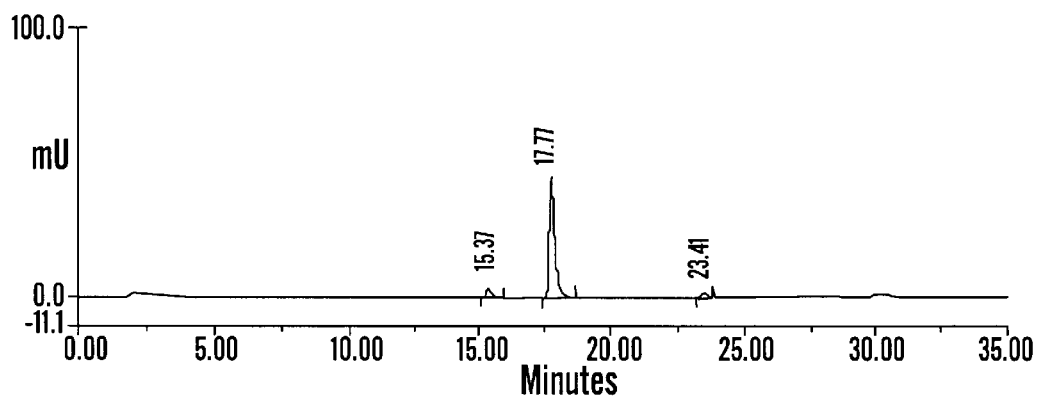
Figure 21:
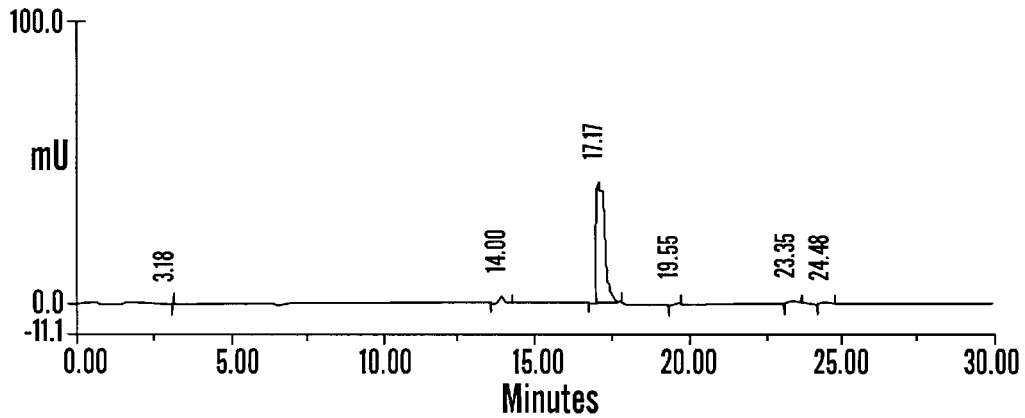
Figure 22:
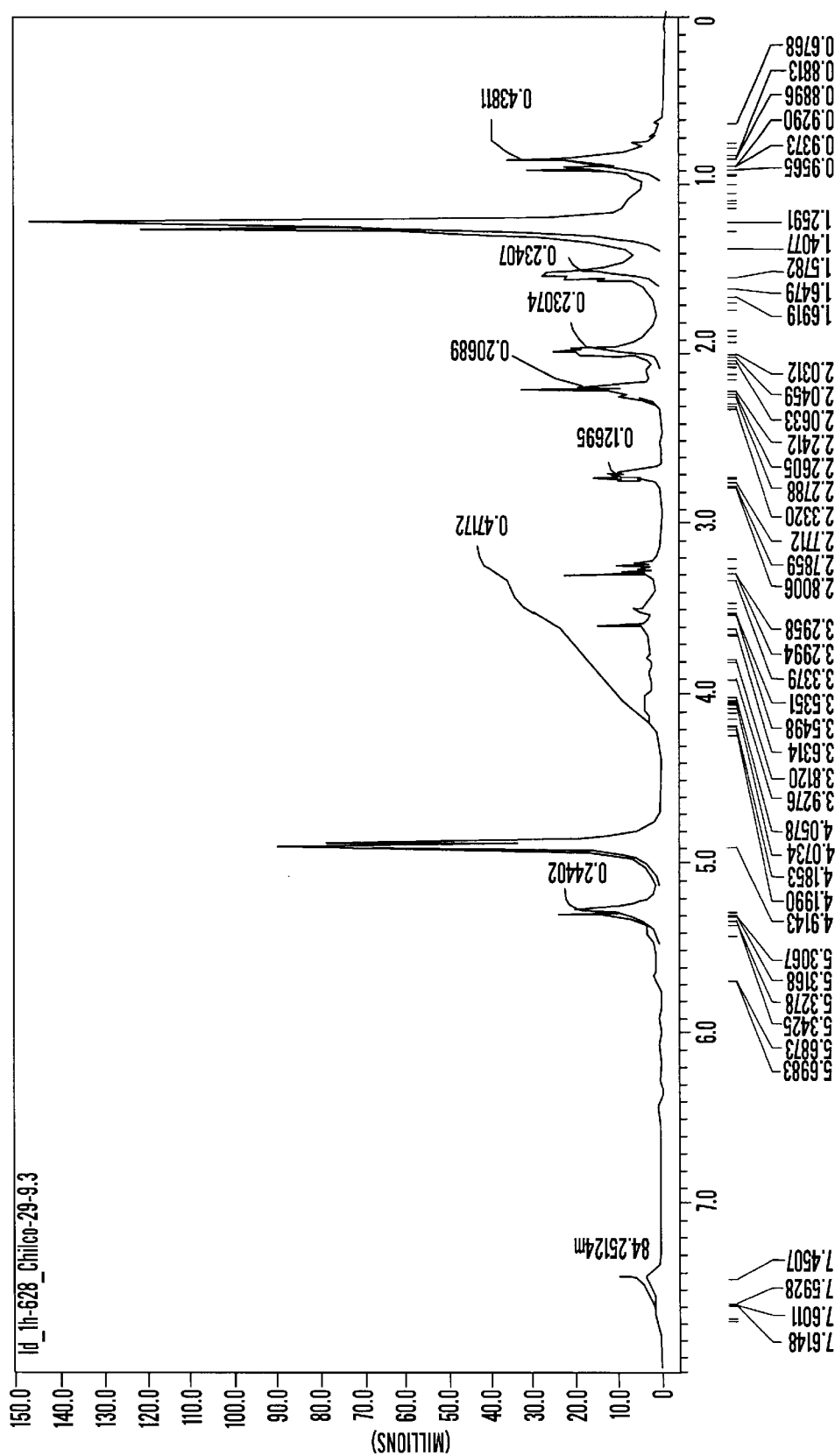

FIG. 14  Mass spectrum of column fraction 4.

Mass spectrum of column fraction 9.

HPLC chromatogram noting the presence of ellagic acid and quercetin in the extract.

Structures of ellagic acid and quercetin

HPLC chromatogram of column fraction 9 and quercetin mixture.

HPLC chromatogram of column fraction 9 at 337nm.

HPLC chromatogram of standard ellagic acid at 337nm.

HPLC chromatogram of column fraction 9 and standard ellagic acid mixture.

$^1$H NMR spectrum of column fraction 9

CHILCO PRODUCT AND METHOD OF MAKING AND USING SAME

RELATED APPLICATIONS

This application claims priority from U.S. Provisional Patent Application No. 60/158,203 filed in Oct. 7, 1999. The entire disclosure of the provisional application is considered to be part of the disclosure of the accompanying application and is hereby incorporated by reference.

FIELD OF THE INVENTION

The present invention is directed to a product comprising compositions of Chilco containing formulations and methods of using the same, and in a particular, to medicinal formulations useful as a diuretic, as a menstruation regulator, and antipyretic.

BACKGROUND OF THE INVENTION

Fuchsia magellanica lam, also known as the Chilean Chilco plant, is an evergreen bush with small, thin fragile branches. Five fleshy, red sepals form a large cup, while the corolla consists of five purple petals that are much smaller than the cup. The flower has eight stamens and a long style that terminates with a four-lobed stigma. The fruit of the Chilco plant is a large berry. The Chilco plant is native to Chile and is commonly found in humid climates, often bordering lakes.

SUMMARY OF THE INVENTION

Formulations made from the Chilco plant are useful in addressing and treating female hormone replacement/balancing needs. Indeed, it is believed that the present invention may act as a female version of the drug Viagra™ to enhance sexual function in both genders, but especially in females.

Acceptable protocols to administer compounds of the present invention in an effective manner include individual dose size, number of doses, frequency of dose administration, and mode of administration. Determination of such protocols can be accomplished by those skilled in the art depending upon a variety of variables, the weight/mass of the animal, the age of the animal, etc. In a preferred embodiment, the present inventive compounds are used to treat human females and administration of the Chilco products to any individual female will be in line with the administration of other similar compounds known in the art. The manner of administration of a particular compound of the present invention can depend upon the particular purpose for the delivery, any carriers associated with the use of the present inventive compounds, the overall health and condition of the recipient and the judgment of the physician or technician administering the compound to the animal and/or patient. Acceptable delivery methods can include parenteral, topical, oral or local administration, such as intra-dermally or by aerosol. Administration in a variety of unit dosage forms will depend upon the method of administration. For example, unit dosage forms suitable for oral administration to the intestinal region of an animal include powders, tablets, pills and capsules. The compounds of the present invention can be administered to any animal, preferably to mammals, and more preferably to human females.

As will be apparent to one of skill in the art, the present compounds can be combined with other known compounds to create various synergistic effects, including improved administration and/or absorption of such compounds by a female.

In one embodiment of the present invention, the Chilco compound of the present invention, in one of its various forms, is administered to a human female to improve the libido of such female. Indeed, formulations containing Chilco compounds can include, but are not limited to, teas, powders, poultices, oils, etc., and can be combined with various other compounds, including food items, for ease of administration. For example, in one embodiment of the present invention, Chilco products of the present invention are combined with food items, such as salad dressings spreads, etc. so that administration of such compounds by an individual is not conspicuous to outside observers.

Chilco compounds of the present invention can be used in a medicinal fashion to regulate menstruation of females, rendering menstruation periods more predictable in length, severity, etc.

Yet another aspect of the present invention is the use of Chilco derived products as anti-pyretic agents. Thus, treatment of fevers, especially for individuals sensitive to other anti-pyretic drugs, is believed to be a particularly useful embodiment of the present invention.

Yet a further embodiment of the present invention includes the use of Chilco derived products as a diuretic, used alone or in combination with other known diuretic compounds.

As described below, various methods can be used to extract useful compounds from the Chilco flower. Of particular interest in the present invention are fractions denoted 3, 4 and 9, whose mass spectrometry/NMR readings are provided below. Each of such fractions contain single compounds of significant purity, the respective molecular weights of compounds in fractions 3, 4 and 5 being 784, 784 and 302, respectively. Fractions 3 and 4 comprise particular polymers in one embodiment, and/or phenolic-based compounds having a strong UV absorbance at 270 nm. As such, fractions 3 and 4 have flavonoid, lignin and tannin type of properties and thus have uses associated therewith.

Fraction 9 has identifying characteristics similar in many ways to quercetin which is believed to be one of the active compounds in Chilco relating to the medicinal uses set forth herein, including use in the increase of a female's hormone replacement balancing needs to increase and enhance sexual function, act as a diuretic, as an anti-pyretic and as a menstruation regulator. Fraction 9 also has particular characteristics of ellagic acid. Thus, in one embodiment of the present invention, an effective female hormone regulating compound of the present invention is selected from the group of quercetin and ellagic acid, and derivatives thereof. In one particular embodiment, a combination of quercetin and ellagic acid forms the active ingredient of the female menstrual regulation compound of the present invention.

In yet another embodiment, the active ingredient of the present inventive compound comprises that contained in fraction 9 as identified by NMR results as set forth below. Thus, one embodiment of the present invention relates to the administration of fraction 9 of the Chilco extract, accomplished using one or more of the methods set forth herein, to a human female to alleviate and/or regulate certain dysfunctions associated with female hormones, including the regulation of menstruation and as a stimulant to a female's libido.

DETAILED DESCRIPTION OF THE PREFERRED EMBODIMENT

Method

Standard Extraction 50.3 g of flowers were crushed and compacted by hand and placed in 1000 ml beaker.

The biomass was soaked in about 600 ml of 70% ethanol. The beaker was covered with foil and allowed to sit for two days, stirring occasionally, at room temperature. The eluate was drained, and the biomass was soaked twice more in about 600 ml of 70% ethanol for about eight hours each. The ethanol was evaporated and the remaining water was removed by freeze drying yielding 19.8 g of purple solids.

Soxhlet Extraction 20.8 g of flowers were crushed and compacted by hand, loaded into a Soxhlet, and 400 ml of 70% ethanol was added to the 1000 ml flask. The Soxhlet extraction lasted for 16 h at until the eluate lost its reddish color. The ethanol was evaporated and the remaining extract was freeze dried yielding 5.8 g of purple solids.

Reextraction of Soxhlet Biomass

It was determined that the Soxhlet biomass was not fully extracted and required further extraction for two reasons: (1) the standard extraction gave a 39.4% yield whereas the Soxhlet extraction only gave a 27.9% yield, and (2) the Soxhlet biomass retained some of its violet color.

The Soxhlet biomass was transferred to a 500 ml beaker and soaked in about 250 ml of 70% ethanol. The beaker was covered with foil and allowed to sit for about eight hours at room temperature. The eluate was drained, and the biomass was soaked once more under the same conditions. The ethanol was then evaporated and the remaining extract was freeze dried yielding 2.3 g of purple solids. This extract was added to the original Soxhlet extract yielding 8.1 g of solids, or 38.9%. Both extracts, the standard and the "Soxhlet", were combined.

Partitioning of Extract

Two different partition experiments were attempted in order to try to separate polar from nonpolar compounds. Each partition fraction was then analyzed by normal and reversed phase TLC. Partitioning allows the concentration of compounds with similar polarity so that material does not get stuck on a column.

1. Dichloromethane/Water Partition 2.48 g of extract was dissolved in 10 ml of water and transferred from a 50 ml beaker to a 60 ml separatory funnel. The beaker was rinsed with 10 ml dichloromethane and transferred to the funnel. It was then shaken to allow proper mixing of the two solvents and allowed to sit for separation. The heavier, brownish yellow dichloromethane layer was drained off, and the water layer was washed twice more with 10 ml dichloromethane. All dichloromethane fractions were combined and washed with 20 ml of water. An emulsion formed that could not be completely eliminated even after placing it in the freezer for about 45 minutes. The water fraction was drained and combined with the previous water fraction. The dichloromethane fraction was evaporated to yield 0.12 g of solids, and the water fraction was freeze dried to yield 1.10 g of an oily solid.

2. Hexane/90% Methanol Partition

The same method was used here as in the previous partition except for the following:

The starting material was 1.49 g of extract

In the first partition, a layer of insoluble material converged at the layer interface that was nonrecoverable Both fractions were evaporated to dryness The hexane fraction yielded 0.01 g of solids and the 90% methanol fraction yielded 1.15 g of solids.

Further work on the partition fractions was terminated for the following reasons: (1) due to the emulsions and insoluble material that formed, low yields resulted; (2) in each partition, almost all of the material concentrated on one fraction; and (3) TLC analysis did not show any great improvement over that of the original extract.

HPLC Analysis of Extract

The extract was analyzed by HPLC on a C18 reversed phase column (250×4.6 mm) and compared to a library of standards. Two different methods were used since there were two major types of compounds (anthocyanins and flavonoids) expected to be found in the Chilco flower.

1. Anthocyanin Method

The extract was compared to an extract that is known to contain numerous anthocyanins. The material was eluted with increasing concentrations of methanol in 0.5% trifluoroacetic acid in a gradient fashion (30–35% methanol, 0–8 min; 35–46% methanol, 8–20 min).

2. Flavonoid Method

Unhydrolyzed and hydrolyzed samples of the extract were compared to an extract that is known to contain numerous flavonoids. The material was eluted with increasing concentrations of acetonitrile in 0.5% trifluoroacetic acid in a gradient fashion (10–50% acetonitrile, 0–40 min).

The chromatograms were observed at 440, 337 and 270 nm to determine the optimal wavelength for detecting the major peak(s). This was determined to be 270 nm. At this wavelength, the one major peak represented a compound that could not be identified in this experiment. Two other peaks at 337 nm were identified as ellagic acid and quercetin, but they were in minor amounts in comparison to the peak at 270 nm.

Column Chromatography of Extract

The extract was run on a C-1 8 reversed phase column in an attempt to isolate the major compound. 12.55 g of extract was dissolved in about 50 ml of water and loaded onto a column packed with about 110 g of C-18 media. Material was eluted with increasing concentrations of methanol in water, and the column was finally washed with 25% dichloromethane in methanol and with acetone. A mass balance of 11.63 g (92.7%) was determined by the 12 fractions collected.

HPLC Analysis of Column Fractions

Analysis and comparison of each column fraction was performed by HPLC. The column fractions were dried by evaporation of the organic solvents and freeze drying of the water. Samples of fractions 2–12 were prepared by dissolving a portion of each fraction and the original extract in an appropriate solvent in a concentration of 10 mg/ml. Fraction 1 was discarded since it did not contain any material. The samples were injected onto a reversed phase C-18 column (250×4.6 mm), eluted with increasing concentrations of acetonitrile in 0.5% trifluoroacetic acid in a gradient fashion (10–50% acetonitrile, 0–30 min) and observed at 270 nm unless otherwise noted. According to the HPLC chromatograms, fractions 3, 4, and 9 contained single compounds ranging from 90–94% purity. Fractions 3 and 4 had very similar retention times and are expected to be the same compound, and they also represented what appeared to be the major peak in the extract.

Mass Analysis of Fractions of Interest

Fractions 3, 4 and 9 were analyzed by mass spectrometry. Electrospray ionization was performed and the mass spectra were continuously acquired in the negative ion mode over a mass range of 100–1000 amu at the rate of 8.0 sec/scan. Fractions 3 and 4 both had masses of 784 amu, and fraction 9 had a mass of 302 amu.

NMR Analysis of Fractions of Interest

Fractions 3, 4 and 9 were analyzed by nuclear magnetic resonance spectroscopy. Fractions 3 and 4 were prepared in water-$d_2$ and fraction 9 was prepared in methanol-$d_4$. Both $^1H$ and $^{13}C$ NMR were obtained.

Materials & Apparatus
1. Starting material: Chilco flower, Fuchsia magellanica Lam., about 125 g
2. Small Soxhlet apparatus with 1000 ml flask
3. Solvents
   Acetone-reagent grade
   Acetonitrile—HPLC grade
   DI water
   Dichloromethane—reagent grade
   Ethanol—reagent grade
   Hexanes—reagent grade
   Methanol—analytical grade
   Trifluoroacetic acid—analytical grade
4. TLC
   Whatman C-18 reversed phases plate with fluorescent indicator
   Whatman silica gel 60A plates with fluorescent indicator
5. Standards
   Bilberry extract
   Rosemary water-soluble extract
6. HPLC
   Hitachi L-6200A Intelligent Pump with L-4500A Diode Array detector and AS-4000 Intelligent Auto Sampler
   Hitachi L-6200 Intelligent Pump with L-4000 UV detector and AS-4000 Intelligent Auto Sampler
   Phenomenex Hypersil C-18 reversed phase column, 5 micron, 250×4.6 mm, P/NO 00G-152-EO
7. Mass Spectrometer
   Hewlett-Packard 1050 Liquid Chromatograph interfaced to a VG Platform Mass Spectrometer
8. NMR Spectrometer
   JEOL 400 MHZ Results Total Extraction
   Starting material: 71. g Chilco flowers
   Yield: 27.9 g extract 939.2%)
Partitioning of Extract
1. Dichloromethane/Water Partition
   Starting Material: 2.48 g extract
   Yields:
      $CH_2CL_2$: 0.12 g (4.8%)
      Water: 1.10 g (44.4%)
2. Hexane/90% Methanol Partition
   Staring Material 1.49 g extract
   Yield:
      Hexane: 0.01 g (0.7%) 90% Methanol: 1.15 g (77.2%)
Column Chromatography of Extract
Starting material: 12.55 g Chilco flower extract

| Fraction | ml Collected | Appearance | Fraction Wt. (g) |
|---|---|---|---|
| 1 | 100 | clear | 0 |
| 2 | 200 | lt. yellow | 6.51 |
| 3 | 200 | yellow | 0.84 |
| 4 | 200 | yellow | 0.81 |

-continued

| Fraction | ml Collected | Appearance | Fraction Wt. (g) |
|---|---|---|---|
| 5 | 200 | lt. red | 1.32 |
| 6 | 200 | red | 1.24 |
| 7 | 200 | red | 0.37 |
| 8 | 200 | red | 0.23 |
| 9 | 200 | red | 0.13 |
| 10 | 200 | yellow/green | 0.06 |
| 11 | 600 | yellow/green | 0.12 |
| 12 | 800 | yellow/green | 0 |

Total Mass Collected: 11.63 g
% Mass Collected: 92.67%
HPLC Analysis of Column Fractions
Fractions 3, 4, and 9 contained single compounds of significant purity. Purity was determined by percent area as a result of peak integration.

| Fraction | Retention Time | Peak Purity |
|---|---|---|
| 3 | 8.93 | 93.7% |
| 4 | 8.25 | 93.1% |
| 9 | 17.05 | 89.6% |

Mass Spectrometry of Fractions 3, 4 and 9
The determined molecular weight of the major compound of each fraction is as follows:

| Fraction | Neg. Ion Result | Molecular Wt. |
|---|---|---|
| 3 | 783 | 784 |
| 4 | 783 | 784 |
| 9 | 301 | 302 |

DISCUSSION

HPLC analysis of a 70% ethanol extract of the Chilco flowers using a diode array detector indicated that ellagic acid and quercetin were present in somewhat minor amounts. It is also revealed the presence of one compound that is by far the major constituent. Column chromatography of the extract gave two adjacent fractions, fractions 3 and 4, that contained this compound in relatively high purity, according to further HPLC analysis. The mass spectra of these fractions disclosed a mass 784 amu for both. $^1H$ and $^{13}C$ NMR are currently in progress to aid in the identification of this compounds. These compounds are believed to be polymers since, upon hydrolysis, the representative peak disappears and others appear. Other components are phenolic, based on strong UV absorbance at 270 nm, indicating a flavonoid, lignin or tannin.

A later fraction, fraction 9, also contained another compound of decent purity. The mass spectrum indicated the mass of this compound as 302 amu. Quercetin is a flavonoid of mass 302 amu and is commonly found in this genus and family. A close comparison, however, of this fraction's chromatogram with the chromatogram that previously identified quercetin in the extract, even though different methods were used, suggested that this unknown compound might not be quercetin. To answer this question, a solution was prepared that partly contained material from this fraction and partly standard quercetin, and this mixture was analyzed by HPLC. Two distinct peaks in the chromatogram at 17.4 and 24.8 min indicated that the compound in this fraction was not quercetin. Ellagic acid, the other identified compound in the extract, also has a mass of 302 amu. A mixture was again prepared, this time with standard ellagic acid, and was analyzed by HPLC. The ellagic acid was already in solution in pyridine; therefore, the sample was analyzed at 337 nm due to pyridine's absorbance at 270 nm. The chromatograms revealed only one peak, thus indicating that fraction 9 is ellagic acid. $^1$H and $^{13}$C NMR were performed but the spectra were not indicative of ellagic acid.

While various embodiments of the present invention have been described in detail, it is apparent that further modifications and adaptations of the invention will occur to those skilled in the art. However, it is to be expressly understood that such modifications and adaptations are within the spirit and scope of the present invention.

Figure 9:
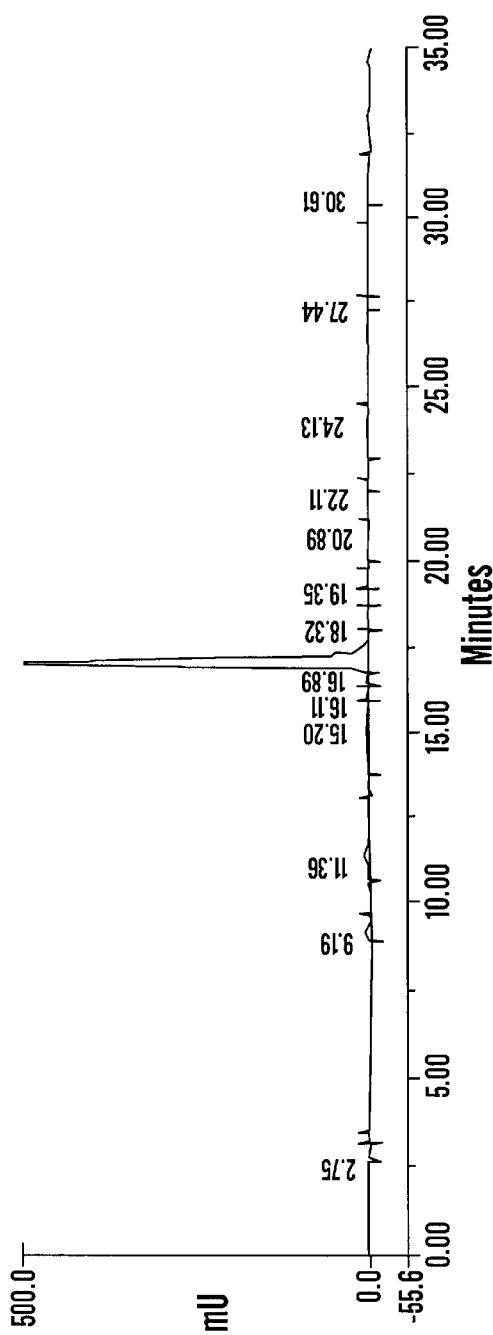
Figure 10:
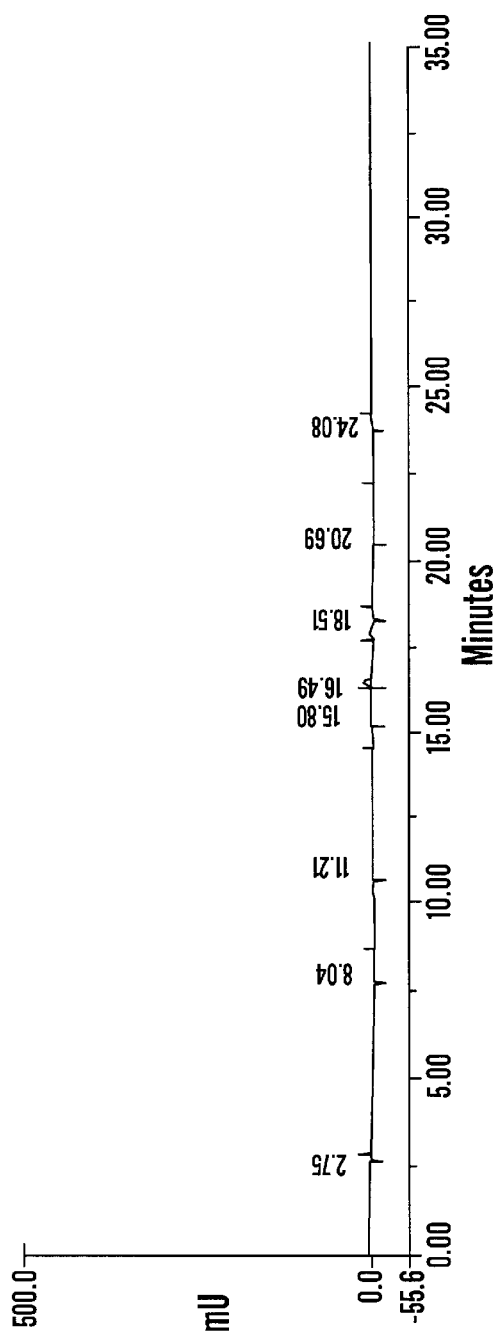
Figure 11:
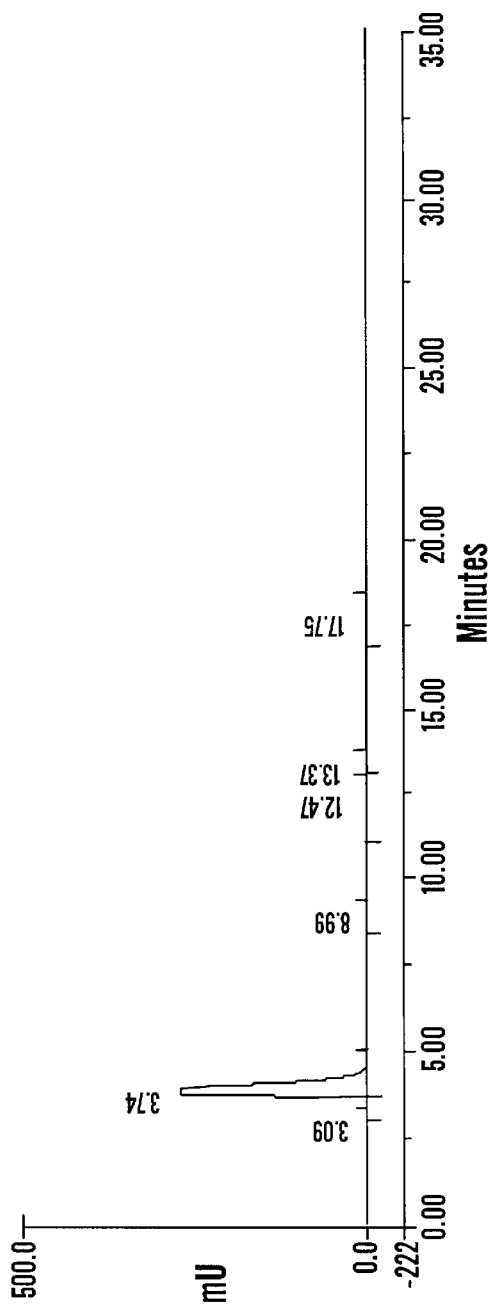
Figure 12:
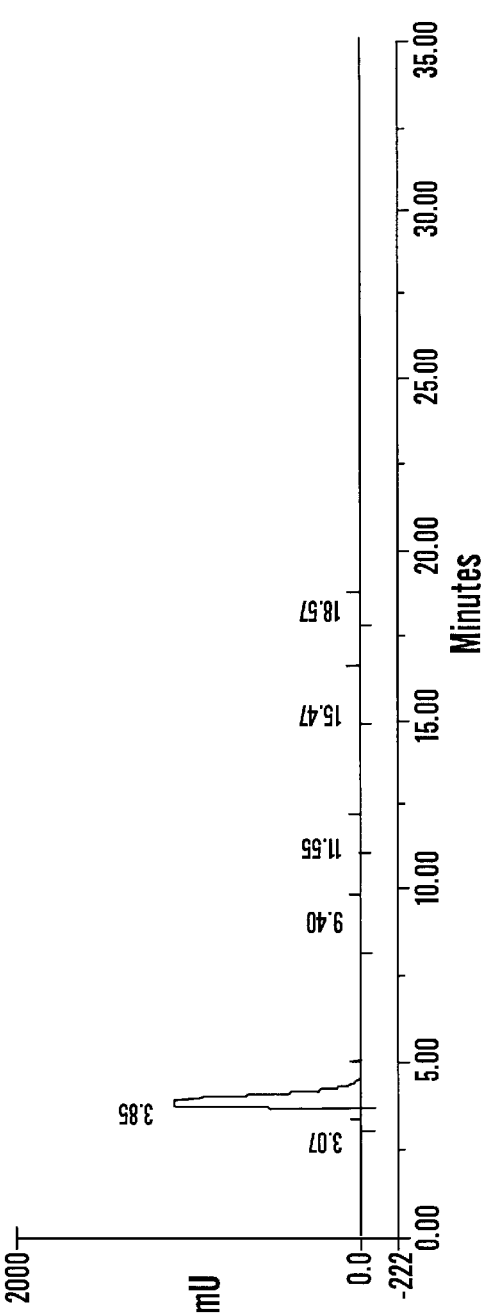
Figure 13:
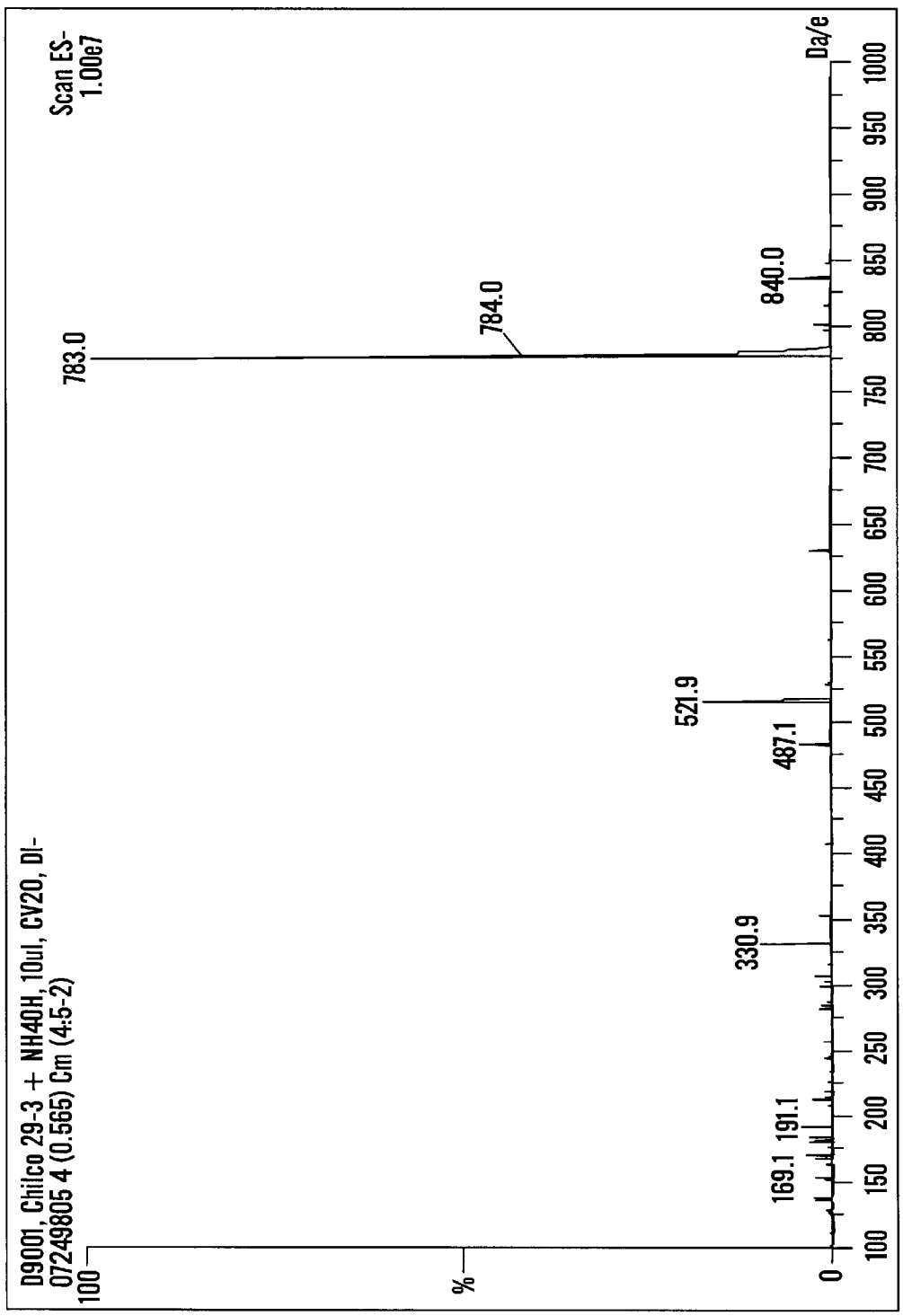

What is claimed is:

1. A formulation effective to regulate female human menstruation, consisting essentially of a composition derived from the Chilco flower, said, composition comprising effective amounts of ellagic acid and quercetin and an isolated fraction raction 9 as set forth in FIG. 9 pursuant to an HPLC chromatogram.

2. A formulation effective to regulate female human menstruation, consisting essentially of a composition derived from the Chilco flower, said composition consisting essentially of effective amounts of ellagic acid and quercetin and an isolated fraction 9 as set forth in FIG. 9 pursuant to an HPLC chromatogram, wherein said formulation is effective in addressing female hormone replacement/balancing needs so as to improve the libido of said female.

3. A formulation as set forth in claim 1, wherein said formulation is administered in the form of a tea.

4. The formulation as set forth in claim 1, wherein said formulation is effective in rendering said female menstruation periods more predictable in length and severity.

5. A method for regulating female human menstruation, consisting essentially of administering to a female a composition derived from the Chilco flower, said composition consisting essentially of effective amounts of ellagic acid and quercetin and an isolated fraction 9 as set forth in FIG. 9 pursuant to an HPLC chromatogram.

* * * * *